(12) United States Patent
Rubin

(10) Patent No.: US 7,652,070 B2
(45) Date of Patent: Jan. 26, 2010

(54) TREATMENT METHOD FOR MMP-IMPLICATED PATHOLOGIES

(76) Inventor: Benjamin Rubin, 7801 Renoir Ct., Potomac, MD (US) 20854

( * ) Notice: Subject to any disclaimer, the term of this patent is extended or adjusted under 35 U.S.C. 154(b) by 34 days.

(21) Appl. No.: 11/695,164

(22) Filed: Apr. 2, 2007

(65) Prior Publication Data

US 2008/0242735 A1   Oct. 2, 2008

(51) Int. Cl.
*A01N 33/08*   (2006.01)
*A61K 9/00*    (2006.01)
(52) U.S. Cl. ..................... 514/665; 424/400
(58) Field of Classification Search ............. 514/665; 424/400
See application file for complete search history.

(56) References Cited

U.S. PATENT DOCUMENTS

2005/0143473 A1 * 6/2005 Wong et al. ............ 514/665

OTHER PUBLICATIONS

Chiba et al., Increase in the expression of matirx metalloproteinase-12 in the airways of rats with allergic bronchial asthma, Feb. 2007, Biol Pharm Bull, 30(2), 318-323- Abstract only presented printed from http://www.ncbi.nlm.nih.gov/pubmed/17268073?ordinalpos=2&itool=EntrezSystem2.PEntrez.Pubmed.Pubmed_ResultsPanel.Pubmed_RVDocSum, 2 pages.*

Sachdev et al., Matrix Metalloproteinases and Tisuue Inhibitors of Matrix Metalloproteinases in the Human Lens: Implications for Cortical Cataract Formation, 2004, Investigative Ophthalmology & Visual Science, 45(11), 4075-4082.*

Hsuan et al., The penetration of topical cysteamine into the human eye, J Ocul Pharmacol Ther., 1996 Winter, 12(4), 499-502- Abstract only presented printed from http://www.ncbi.nlm.nih.gov/pubmed/8951686?ordinalpos=5&itool=EntrezSystem2.PEntrez.Pubmed.Pubmed_ResultsPanel.Pubmed_RVDocSum, 1 page.*

Iwata et al., A Randomized Clinical Trial of Topical Cysteamine Disulfide (Cystamine) versus Free Thiol (Cysteamine) in the Treatment of Corneal Cystine Crystals in Cystinosis, Aug. 1998, Molecular Genetics and Metabolism, vol. 64, Issue 4, 237-242.*

* cited by examiner

*Primary Examiner*—Frederick Krass
*Assistant Examiner*—Gigi Huang
(74) *Attorney, Agent, or Firm*—Jeffrey Weiss; Weiss & Moy, P.C.

(57) ABSTRACT

A treatment method for pathologies in which increased levels of MMP production are implicated in pathogenesis. Examples of such pathologies include pterygium, keratoconus, and macular degeneration. Treatment is based on administration of cysteamine in therapeutically effective amounts. Treatment may be in one of several alternative forms, including eye drops and oral applications. Administration in the form of eye drops may be preferred for pathologies affecting the eyes.

5 Claims, 1 Drawing Sheet

TREATMENT METHOD FOR MMP-IMPLICATED PATHOLOGIES

GOVERNMENTAL INTEREST

The present invention was made with support from the National Institutes of Health. Consequently, the government retains certain rights in the invention.

FIELD OF THE INVENTION

The present invention relates to treatment methods for pathologies in which elevated MMP production is implicated in pathogenesis.

BACKGROUND OF THE INVENTION

A pterygium is an elevated, superficial, external ocular mass that usually forms over the cornea, and particularly in Bowman's layer. Pterygia can vary from small, atrophic quiescent lesions to large, aggressive, rapidly growing fibrovascular lesions that can distort the corneal topography, and, in advanced cases, obscure the optical center of the cornea. Growth is typically in a triangular shape.

The pathophysiology of pterygia is characterized by degeneration of collagen and fibrovascular proliferation, with an overlying covering of epithelium. It is believed that pterygium cells may produce elevated levels of matrix metallopeptidase (MMP), including specifically MMP-1, MMP-2, and MMP-9. Proteins of the MMP family are involved in the breakdown of extracellular matrix in normal physiological processes, such as embryonic development, reproduction, and tissue remodeling. It is believed that the over-expressed MMP's are responsible for the dissolution of Bowman's layer.

Occurrence of ptyerigium varies with geographical location. Within the continental United States, prevalence rates vary from less than 2% above the 40th parallel to 5-15% in latitudes between 28-36°. Outside of the U.S., a similar relationship is seen between incidence of pterygium and geographical location. There is a relatively high incidence of pterygium in the countries of the Middle East. A relationship is thought to exist between increased prevalence of pterygium and elevated levels of ultraviolet light exposure in the lower latitudes. There may also be a genetic predisposition to the formation of pterygia.

Pterygia can cause a significant alteration in visual function in advanced cases. They also can become inflamed, resulting in redness and ocular irritation. Medical therapy of inflammation-causing pterygia consists of application of over-the-counter artificial tears/topical lubricating drops (eg, Refresh Tears®, GenTeal® drops) and/or bland, non-preserved ointments (eg, Refresh P.M.®, Hypo Tears®), as well as occasional short-term use of topical corticosteroid anti-inflammatory drops (eg, Pred Forte® 1%) when symptoms are more intense. However, such treatments address the inflammation symptoms only, and do not interfere with the growth of the pterygium. A pterygium that is large enough to impair sight or is unsightly may need to be removed surgically.

Pterygium is one example of a pathology associated with increased MMP production. Other such pathologies include Kerataconus, macular degeneration, corneal melting, occlusions in the choroid, cancer and heart disease.

A need exists for a non-surgical treatment for pterygium and other MMP-implicated pathologies, as well as a less toxic adjunct for pterygium, glaucoma and vitreo-retinal membranes}

SUMMARY OF THE INVENTION

In accordance with one embodiment of the present invention, a method for treating a host having a pathology in which increased production of MMP is implicated is disclosed. The method comprises: administering to a host having a pathology in which increased production of MMP is implicated a composition including cysteamine.

In accordance with another embodiment of the present invention, a method for treating a host having a pathology in which increased production of MMP is implicated is disclosed. The method comprises: administering to a host having a pathology in which increased production of MMP is implicated a composition including cysteamine; wherein the pathology is pterygium; and wherein the step of administering cysteamine comprises providing cysteamine in the form of eye drops.

In accordance with another embodiment of the present invention, a method for treating a host having a pathology in which increased production of MMP is implicated is disclosed. The method comprises: administering to a host having a pathology in which increased production of MMP is implicated a composition including cysteamine; wherein the pathology is pterygium; wherein the step of administering cysteamine comprises providing cysteamine in the form of eye drops; wherein the eye drops are provided between about two and twelve times per day; and wherein the concentration of cysteamine in the composition in between about 0.1% and about 0.5%.

DETAILED DESCRIPTION OF THE PREFERRED EMBODIMENTS

Figure 1:
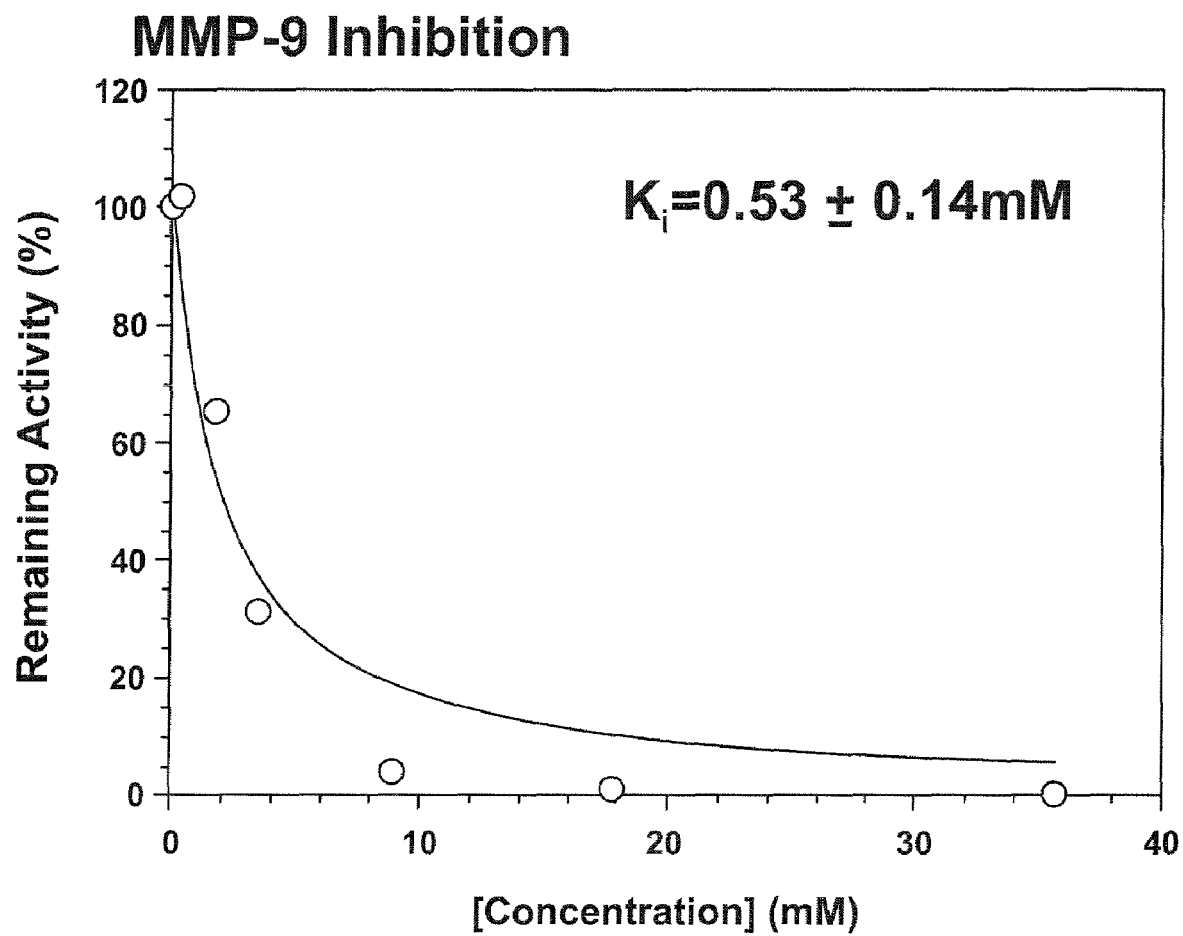
FIG. 1 is a table illustrating inhibition of MMP-9 by cysteamine.

Generally, the nomenclature used hereafter is that which is well known and commonly employed in the art. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For the purposes of the present invention, the foregoing terms are defined below.

Cysteamine ($HSCH_2CH_2NH_2$) is a stable aminothiol and a degradation product of the amino acid cysteine. Under the trade name Cystagon®, cysteamine is used in the treatment of disorders of cystine excretion, such as cystinosis. Cystinosis patients precipitate crystals of cysteine throughout the body, including particularly in the eye and kidney. Cysteamine cleaves the disulfide bond with cysteine to produce molecules that can escape the metabolic defect in cystinosis patients.

Cysteamine {HCl} is currently provided to cystinosis patients in an oral/systemic form or as an eye drop, at a concentration level of 0.5% and in a solution preserved with benzalkonium. (It should be noted that concentrations of 0.1% have been shown to be effective.) For the eye drop application, patients may be advised to use the drops as many as 12 times per day. While there may be a slight burning sensation as the drops enter the eye, no toxicity has not been observed. Oral cysteamine {bitartrate} is generally recommended where there is an impairment of renal function. Cysteamine therapy has been shown to produce improved growth and stabilized renal function in pre-renal transplant cystinotics, without substantial toxicity. Cysteamine is manufactured by Sigma-Tau Pharmaceuticals, Inc., and is currently provided to Cystinosis patients under IND 40593.

FIG. 1 illustrates the result of a laboratory test showing the breakdown of MMP-9 as analyzed by zymography. Because enzymes are structure specific, it can be inferred that there is inhibition of MMP-9 by cysteamine. It is believed that cysteamine inactivates MMP by breaking an important sulfur bond, causing the enzyme to unfold. As shown in FIG. 1, increased concentrations of cysteamine break down MMP-9 following Michaelis-Mentin kinetics, with a $K_i$ of $0.53\pm0.14$ mM. It is assumed that cysteamine would similarly inhibit other MMP's implicated in pterygium pathogenesis, including specifically MMP-1 and MMP-2.

According to one embodiment of the present invention, pterygia may be treated by administration of cysteamine. In one embodiment, cysteamine may be provided in either of the forms currently used in the treatment of cystinosis—i.e., either in the form of an eye drop or orally, and in the concentrations and formulations previously utilized. Other therapeutically beneficial formulations and/or concentrations of cysteamine may also be provided.

Where cysteamine is to be applied by eye drops, application multiple times per day may be desired. In one embodiment, application may occur four times per day. However, fewer applications may provide some beneficial results, and a greater number of applications may provide improved efficacy. It should be noted that applications of cysteamine drops 12 times per day has been prescribed for some cystinosis patients.

In one embodiment, cysteamine is used in the treatment of pterygium. Applicant notes that pterygium represents an example of a pathology in which excess MMP production is implicated in pathogenesis. Kerataconus and macular degeneration are examples of other pathologies affecting the eye in which MMP is also implicated. Cysteamine therapy, as described herein, may also be utilized in the treatment of keratoconus and/or macular degeneration, with a topical application involving eye drops being one preferred treatment method. Cysteamine therapy may also be provided in the treatment of conditions causing corneal melting, including auto-immune disease, inflammation and infection. Similarly, cysteamine therapy may be provided for the treatment of subretinal/choroidal neovascular membrane. Using this as an adjunct treatment may reduce the incidence of occlusions in the choroid, produced as a side effect of the use of Avantis® and/or Lucentis® as an antibody against VEGF.

Cysteamine may also be used after glaucoma surgery, trabeculectomy or seton, to reduce scar tissue proliferation. By inhibiting MMP production at a specific time in the healing process, it is possible that scar tissue which can cause the surgery to fail will be minimized.

Further, it should be noted that other pathologies also are accompanied by excess MMP production. These include certain cancers which use MMP's to spread and certain types of heart disease. Cysteamine may be provided as an effective therapy for such pathologies, with an oral/systemic application being considered preferred for pathologies that manifest themselves in places other than the eye.

It should be noted that the quantity of cysteamine necessary for effective therapy will depend on many different factors, including means of administration, target site, physiological state of the patient, and other medicaments administered. Thus, treatment dosages should be titrated to optimize safety and efficacy. Typically, dosages used in vitro may provide useful guidance in the amounts useful for in situ administration of the active ingredients in a quantity sufficient to constitute a therapeutic dose. Animal testing of effective doses for treatment of particular disorders will provide further predictive indication of a human therapeutic dosage. Various considerations are described, for example, in Goodman and Gilman's The Pharmacological Basis of Therapeutics, 7th Edition (1985), MacMillan Publishing Company, New York, and Remington's Pharmaceutical Sciences 18th Edition, (1990) Mack Publishing Co, Easton, Pa. Methods for administration are discussed therein, including oral, intravenous, intraperitoneal, intramuscular, transdermal, nasal, iontophoretic administration, and the like.

Unit dosage forms suitable for oral administration include solid dosage forms such as powder, tablets, pills, and capsules, and internally consumable liquid dosage forms, such as elixirs, gums, liquids, syrups, and suspensions. Gelatin capsules may contain the active ingredient and as therapeutically acceptable inactive ingredients powdered carriers, such as glucose, lactose, sucrose, mannitol, starch, cellulose or cellulose derivatives, magnesium stearate, stearic acid, sodium saccharin, talcum, magnesium carbonate and the like. Examples of additional pharmaceutically acceptable inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

For solid compositions, conventional, nontoxic, therapeutically acceptable, solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more compositions of the invention of the invention, and more preferably at a concentration of 25%-75%.

The concentration of the compositions of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

Any of the foregoing formulations may be appropriate in treatments and therapies in accordance with the present invention, provided that the active agent in the formulation is not inactivated by the formulation and the formulation is physiologically compatible.

Although particular embodiments of the invention have been described in detail for purposes of illustration, various modifications may be made without departing from the spirit and scope of the invention. Accordingly, the invention is not to be limited, except as by the appended claims.

I claim:
1. A method for treating a host having pterygium, comprising:
   administering to a host having pterygium a composition including cysteamine ($HSCH_2CH_2NH_2$); and wherein the step of administering cysteamine comprises providing cysteamine in the form of eye drops; and thereby treating the pterygium.

2. The method of claim 1 wherein the eye drops are provided between about two and twelve times per day.

3. The method of claim 1 wherein the concentration of cysteamine in the composition from about 0.1% and about 0.5%.

4. The method of claim 3 wherein the concentration of cysteamine in the composition is about 0.5%.

5. A method for treating a host having pterygium, comprising:

administering to a host having pterygium a composition including cysteamine ($HSCH_2CH_2NH_2$);

wherein the step of administering cysteamine comprises providing cysteamine in the form of eye drops;

wherein the eye drops are provided between about two and twelve times per day; and wherein the concentration of cysteamine in the composition in between about 0.1% and about 0.5%; and thereby treating the pterygium.

\* \* \* \* \*